(12) United States Patent
Andrews et al.

(10) Patent No.: US 9,283,683 B2
(45) Date of Patent: Mar. 15, 2016

(54) VENTILATED VACUUM COMMUTATION STRUCTURES

(71) Applicant: Curt G. Joa, Inc., Sheboygan Falls, WI (US)

(72) Inventors: Robert E. Andrews, Sheboygan, WI (US); Gottfried Jason Hohm, Sheboygan Falls, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 0 days.

(21) Appl. No.: 14/261,072

(22) Filed: Apr. 24, 2014

(65) Prior Publication Data

US 2015/0028612 A1    Jan. 29, 2015

Related U.S. Application Data

(60) Provisional application No. 61/857,905, filed on Jul. 24, 2013.

(51) Int. Cl.
*B65G 47/24* (2006.01)
*B25J 15/06* (2006.01)
*A61F 13/15* (2006.01)

(52) U.S. Cl.
CPC ....... *B25J 15/0616* (2013.01); *A61F 13/15764* (2013.01)

(58) Field of Classification Search
CPC ............................. B65G 47/843; B65G 47/244
USPC .................. 198/377.04, 377.08, 471.1, 482.1
See application file for complete search history.

(56) References Cited

U.S. PATENT DOCUMENTS

| | | | |
|---|---|---|---|
| 135,145 A | 1/1873 | Murphy |
| 293,353 A | 2/1884 | Purvis |
| 312,257 A | 2/1885 | Cotton et al. |
| 410,123 A | 8/1889 | Stilwell |
| 432,742 A | 7/1890 | Stanley |
| 643,821 A | 2/1900 | Howlett |
| 1,393,524 A | 10/1921 | Grupe |
| 1,431,315 A | 10/1922 | Le Moine |
| 1,605,842 A | 11/1926 | Jones |
| 1,686,595 A | 10/1928 | Belluche |
| 1,957,651 A | 5/1934 | Joa |
| 2,009,857 A | 7/1935 | Potdevin |
| 2,054,832 A | 9/1936 | Potdevin |
| 2,117,432 A | 5/1938 | Linscott |

(Continued)

FOREIGN PATENT DOCUMENTS

| | | |
|---|---|---|
| BE | 1007854 | 11/1995 |
| CA | 1146129 | 5/1983 |

(Continued)

OTHER PUBLICATIONS

European Search Report, related to EP patent application No. 14178233, dated Nov. 6, 2014, 7 pages.

*Primary Examiner* — Douglas Hess
(74) *Attorney, Agent, or Firm* — Ryan Kromholz & Manion, S.C.

(57) ABSTRACT

Ventilated vacuum structures such as pucks and rings are disclosed for carrying portions of disposable products during manufacturing. Air flow enters vacuum commutation ports on an article carrying structure from vents nearby, the vents receiving air from a side, a top or an underside of the article carrying structure.

7 Claims, 9 Drawing Sheets

(56) References Cited

U.S. PATENT DOCUMENTS

| | | |
|---|---|---|
| 2,128,746 A | 8/1938 | Joa |
| 2,131,808 A | 10/1938 | Joa |
| 2,164,408 A | 7/1939 | Joa |
| 2,167,179 A | 7/1939 | Joa |
| 2,171,741 A | 9/1939 | Cohn et al. |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,627,859 A | 2/1953 | Hargrave |
| 2,695,025 A | 11/1954 | Andrews |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,788,786 A | 4/1957 | Dexter |
| 2,811,905 A | 11/1957 | Kennedy, Jr. |
| 2,828,745 A | 4/1958 | Deutz |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,890,700 A | 6/1959 | Lonberg-Holm |
| 2,913,862 A | 11/1959 | Sabee |
| 2,939,461 A | 6/1960 | Joa |
| 2,939,646 A | 6/1960 | Stone |
| 2,960,143 A | 11/1960 | Joa |
| 2,990,081 A | 6/1961 | De Neui et al. |
| 2,991,739 A | 7/1961 | Joa |
| 3,016,207 A | 1/1962 | Comstock, III |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,075,684 A | 1/1963 | Rothmann |
| 3,086,253 A | 4/1963 | Joa |
| 3,087,689 A | 4/1963 | Heim |
| 3,089,494 A | 5/1963 | Schwartz |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,318,608 A | 5/1967 | Smrekar |
| 3,322,589 A | 5/1967 | Joa |
| 3,336,847 A | 8/1967 | Durat |
| 3,342,184 A | 9/1967 | Joa |
| 3,356,092 A | 12/1967 | Joa |
| 3,360,103 A | 12/1967 | Joa |
| 3,391,777 A | 7/1968 | Joa |
| 3,454,442 A | 7/1969 | Heller, Jr. |
| 3,463,413 A | 8/1969 | Smith |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,527,123 A | 9/1970 | Dovey |
| 3,538,551 A | 11/1970 | Joa |
| 3,540,641 A | 11/1970 | Besnyo |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger et al. |
| 3,728,191 A | 4/1973 | Wierzba et al. |
| 3,745,947 A | 7/1973 | Brocklehurst |
| 3,751,224 A | 8/1973 | Wackerle |
| 3,758,102 A | 9/1973 | Munn et al. |
| 3,762,542 A | 10/1973 | Grimes |
| 3,772,120 A | 11/1973 | Radzins |
| 3,776,798 A | 12/1973 | Milano |
| 3,796,360 A | 3/1974 | Alexeff |
| 3,810,344 A | 5/1974 | Evans et al. |
| 3,811,987 A | 5/1974 | Wilkinson et al. |
| 3,816,210 A | 6/1974 | Aoko et al. |
| 3,836,089 A | 9/1974 | Riemersma |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,901,238 A | 8/1975 | Geller et al. |
| 3,903,768 A | 9/1975 | Amberg et al. |
| 3,904,147 A | 9/1975 | Taitel et al. |
| 3,918,698 A | 11/1975 | Coast |
| 3,921,481 A | 11/1975 | Fleetwod |
| 3,941,038 A | 3/1976 | Bishop |
| 3,960,646 A | 6/1976 | Wiedamann |
| 3,988,194 A | 10/1976 | Babcock et al. |
| 3,991,994 A | 11/1976 | Farish |
| 4,002,005 A | 1/1977 | Mueller et al. |
| 4,003,298 A | 1/1977 | Schott, Jr. |
| 4,009,626 A | 3/1977 | Gressman |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,220,237 A | 9/1980 | Mohn |
| 4,222,533 A | 9/1980 | Pongracz |
| 4,223,822 A | 9/1980 | Clitheroe |
| 4,231,129 A | 11/1980 | Winch |
| 4,234,157 A | 11/1980 | Hodgeman et al. |
| 4,236,955 A | 12/1980 | Prittie |
| 4,275,510 A | 6/1981 | George |
| 4,284,454 A | 8/1981 | Joa |
| 4,297,157 A | 10/1981 | Van Vilet |
| 4,307,800 A | 12/1981 | Joa |
| 4,316,756 A | 2/1982 | Wilson |
| 4,325,519 A | 4/1982 | McLean |
| 4,331,418 A | 5/1982 | Klebe |

(56) References Cited

U.S. PATENT DOCUMENTS

| | | |
|---|---|---|
| 4,342,206 A | 8/1982 | Rommel |
| 4,349,140 A | 9/1982 | Passafiume |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,426,897 A | 1/1984 | Littleton |
| 4,452,597 A | 6/1984 | Achelpohl |
| 4,479,836 A | 10/1984 | Dickover et al. |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,543,152 A | 9/1985 | Nozaka |
| 4,551,191 A | 11/1985 | Kock et al. |
| 4,578,052 A | 3/1986 | Engel et al. |
| 4,578,133 A | 3/1986 | Oshefsky et al. |
| 4,586,199 A | 5/1986 | Birring |
| 4,587,790 A | 5/1986 | Muller |
| 4,589,945 A | 5/1986 | Polit |
| 4,603,800 A | 8/1986 | Focke et al. |
| 4,606,964 A | 8/1986 | Wideman |
| 4,608,115 A | 8/1986 | Schroth et al. |
| 4,610,681 A | 9/1986 | Strohbeen et al. |
| 4,610,682 A | 9/1986 | Kopp |
| 4,614,076 A | 9/1986 | Rathemacher |
| 4,619,357 A | 10/1986 | Radzins et al. |
| 4,625,612 A | 12/1986 | Oliver |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,173 A | 3/1987 | Johnson et al. |
| 4,650,406 A | 3/1987 | Peters |
| 4,650,530 A | 3/1987 | Mahoney et al. |
| 4,663,220 A | 5/1987 | Wisneski et al. |
| 4,672,705 A | 6/1987 | Bors et al. |
| 4,675,016 A | 6/1987 | Meuli et al. |
| 4,675,062 A | 6/1987 | Instance |
| 4,675,068 A | 6/1987 | Lundmark |
| 4,686,136 A | 8/1987 | Homonoff et al. |
| 4,693,056 A | 9/1987 | Raszewski |
| 4,701,239 A | 10/1987 | Craig |
| 4,707,970 A | 11/1987 | Labombarde et al. |
| 4,720,415 A | 1/1988 | Vander Wielen et al. |
| 4,723,698 A | 2/1988 | Schoonderbeek |
| 4,726,725 A | 2/1988 | Baker et al. |
| 4,726,874 A | 2/1988 | Van Vliet |
| 4,726,876 A | 2/1988 | Tomsovic, Jr. |
| 4,743,241 A | 5/1988 | Igaue et al. |
| 4,751,997 A | 6/1988 | Hirsch |
| 4,753,429 A | 6/1988 | Irvine et al. |
| 4,756,141 A | 7/1988 | Hirsch et al. |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,782,647 A | 11/1988 | Williams et al. |
| 4,785,986 A | 11/1988 | Daane et al. |
| 4,795,416 A | 1/1989 | Cogswell et al. |
| 4,795,451 A | 1/1989 | Buckley |
| 4,795,510 A | 1/1989 | Wittrock et al. |
| 4,798,353 A | 1/1989 | Peugh |
| 4,801,345 A | 1/1989 | Dussaud et al. |
| 4,802,570 A | 2/1989 | Hirsch et al. |
| 4,826,499 A | 5/1989 | Ahr |
| 4,840,609 A | 6/1989 | Jones et al. |
| 4,845,964 A | 7/1989 | Bors et al. |
| 4,864,802 A | 9/1989 | D'Angelo |
| 4,873,813 A | 10/1989 | Labombarde et al. |
| 4,880,102 A | 11/1989 | Indrebo |
| 4,888,231 A | 12/1989 | Angstadt |
| 4,892,536 A | 1/1990 | Des Marais et al. |
| 4,904,440 A | 2/1990 | Angstadt |
| 4,908,175 A | 3/1990 | Angstadt |
| 4,909,019 A | 3/1990 | Delacretaz et al. |
| 4,909,697 A | 3/1990 | Bernard et al. |
| 4,915,767 A | 4/1990 | Rajala et al. |
| 4,917,746 A | 4/1990 | Kons |
| 4,925,520 A | 5/1990 | Beaudoin et al. |
| 4,927,322 A | 5/1990 | Schweizer et al. |
| 4,927,486 A | 5/1990 | Fattal et al. |
| 4,927,582 A | 5/1990 | Bryson |
| 4,937,887 A | 7/1990 | Schreiner |
| 4,963,072 A | 10/1990 | Miley et al. |
| 4,987,940 A | 1/1991 | Straub et al. |
| 4,994,010 A | 2/1991 | Doderer-Winkler |
| 5,000,806 A | 3/1991 | Merkatoris et al. |
| 5,007,522 A | 4/1991 | Focke et al. |
| 5,021,111 A | 6/1991 | Swenson |
| 5,025,910 A | 6/1991 | Lasure et al. |
| 5,029,505 A | 7/1991 | Holliday |
| 5,045,039 A | 9/1991 | Bay |
| 5,045,135 A | 9/1991 | Meissner et al. |
| 5,062,597 A | 11/1991 | Martin et al. |
| 5,064,179 A | 11/1991 | Martin |
| 5,064,492 A | 11/1991 | Friesch |
| 5,080,741 A | 1/1992 | Nomura et al. |
| 5,094,658 A | 3/1992 | Smithe et al. |
| 5,096,532 A | 3/1992 | Neuwirth et al. |
| 5,108,017 A | 4/1992 | Adamski, Jr. et al. |
| 5,109,767 A | 5/1992 | Nyfeler et al. |
| 5,110,403 A | 5/1992 | Ehlert |
| 5,114,392 A | 5/1992 | McAdam et al. |
| 5,127,981 A | 7/1992 | Straub et al. |
| 5,131,525 A | 7/1992 | Musschoot |
| 5,131,901 A | 7/1992 | Moll |
| 5,133,511 A | 7/1992 | Mack |
| 5,147,487 A | 9/1992 | Nomura et al. |
| 5,163,594 A | 11/1992 | Meyer |
| 5,171,239 A | 12/1992 | Igaue et al. |
| 5,176,244 A | 1/1993 | Radzins et al. |
| 5,183,252 A | 2/1993 | Wolber et al. |
| 5,188,627 A | 2/1993 | Igaue et al. |
| 5,190,234 A | 3/1993 | Ezekiel |
| 5,195,684 A | 3/1993 | Radzins |
| 5,203,043 A | 4/1993 | Riedel |
| 5,213,645 A | 5/1993 | Nomura et al. |
| 5,222,422 A | 6/1993 | Benner, Jr. et al. |
| 5,223,069 A | 6/1993 | Tokuno et al. |
| 5,226,992 A | 7/1993 | Morman |
| 5,246,433 A | 9/1993 | Hasse et al. |
| 5,252,228 A | 10/1993 | Stokes |
| 5,267,933 A | 12/1993 | Precoma |
| 5,273,228 A | 12/1993 | Yoshida |
| 5,275,076 A | 1/1994 | Greenwalt |
| 5,275,676 A | 1/1994 | Rooyakkers et al. |
| 5,308,345 A | 5/1994 | Herrin |
| 5,328,438 A | 7/1994 | Crowley |
| 5,334,446 A | 8/1994 | Quantrille et al. |
| 5,340,424 A | 8/1994 | Matsushita |
| 5,353,909 A | 10/1994 | Mukai et al. |
| 5,368,893 A | 11/1994 | Sommer et al. |
| 5,389,173 A | 2/1995 | Merkatoris et al. |
| 5,393,360 A | 2/1995 | Bridges et al. |
| 5,407,507 A | 4/1995 | Ball |
| 5,407,513 A | 4/1995 | Hayden et al. |
| 5,410,857 A | 5/1995 | Utley |
| 5,415,649 A | 5/1995 | Watanabe et al. |
| 5,417,132 A | 5/1995 | Cox et al. |
| 5,421,924 A | 6/1995 | Ziegelhoffer et al. |
| 5,424,025 A | 6/1995 | Hanschen et al. |
| 5,429,576 A | 7/1995 | Doderer-Winkler |
| 5,435,802 A | 7/1995 | Kober |
| 5,435,971 A | 7/1995 | Dyckman |
| 5,449,353 A | 9/1995 | Watanabe et al. |
| 5,464,401 A | 11/1995 | Hasse et al. |
| 5,472,153 A | 12/1995 | Crowley et al. |
| 5,486,253 A | 1/1996 | Otruba |
| 5,494,622 A | 2/1996 | Heath et al. |
| 5,500,075 A | 3/1996 | Herrmann |
| 5,513,936 A | 5/1996 | Dean |
| 5,516,392 A | 5/1996 | Bridges et al. |

(56) References Cited

U.S. PATENT DOCUMENTS

| | | |
|---|---|---|
| 5,518,566 A | 5/1996 | Bridges et al. |
| 5,525,175 A | 6/1996 | Blenke et al. |
| 5,531,850 A | 7/1996 | Herrmann |
| 5,540,647 A | 7/1996 | Weiermann et al. |
| 5,540,796 A | 7/1996 | Fries |
| 5,545,275 A | 8/1996 | Herrin et al. |
| 5,545,285 A | 8/1996 | Johnson |
| 5,552,013 A | 9/1996 | Ehlert et al. |
| 5,555,786 A | 9/1996 | Fuller |
| 5,556,246 A | 9/1996 | Broshi |
| 5,556,360 A | 9/1996 | Kober et al. |
| 5,556,504 A | 9/1996 | Rajala et al. |
| 5,560,793 A | 10/1996 | Ruscher et al. |
| 5,575,187 A | 11/1996 | Dieterlen |
| 5,582,497 A | 12/1996 | Noguchi |
| 5,586,964 A | 12/1996 | Chase |
| 5,602,747 A | 2/1997 | Rajala |
| 5,603,794 A | 2/1997 | Thomas |
| 5,624,420 A | 4/1997 | Bridges et al. |
| 5,624,428 A | 4/1997 | Sauer |
| 5,628,738 A | 5/1997 | Suekane |
| 5,634,917 A | 6/1997 | Fujioka et al. |
| 5,636,500 A | 6/1997 | Gould |
| 5,643,165 A | 7/1997 | Klekamp |
| 5,643,396 A | 7/1997 | Rajala et al. |
| 5,645,543 A | 7/1997 | Nomura et al. |
| 5,659,229 A | 8/1997 | Rajala |
| 5,660,657 A | 8/1997 | Rajala et al. |
| 5,660,665 A | 8/1997 | Jalonen |
| 5,683,376 A | 11/1997 | Kato et al. |
| 5,683,531 A | 11/1997 | Roessler et al. |
| 5,685,873 A | 11/1997 | Bruemmer |
| RE35,687 E | 12/1997 | Igaue et al. |
| 5,693,165 A | 12/1997 | Schmitz |
| 5,699,653 A | 12/1997 | Hartman et al. |
| 5,705,013 A | 1/1998 | Nease |
| 5,707,470 A | 1/1998 | Rajala et al. |
| 5,711,832 A | 1/1998 | Glaug et al. |
| 5,725,518 A | 3/1998 | Coates |
| 5,725,714 A | 3/1998 | Fujioka |
| 5,743,994 A | 4/1998 | Roessler et al. |
| 5,745,922 A | 5/1998 | Rajala et al. |
| 5,746,869 A | 5/1998 | Hayden et al. |
| 5,749,989 A | 5/1998 | Linman et al. |
| 5,759,340 A | 6/1998 | Boothe et al. |
| 5,766,389 A | 6/1998 | Brandon et al. |
| 5,766,411 A | 6/1998 | Wilson |
| 5,779,689 A | 7/1998 | Pfeifer et al. |
| 5,788,797 A | 8/1998 | Herrin et al. |
| 5,817,199 A | 10/1998 | Brennecke et al. |
| 5,827,259 A | 10/1998 | Laux et al. |
| 5,829,164 A | 11/1998 | Kotischke |
| 5,836,931 A | 11/1998 | Toyoda et al. |
| 5,858,012 A | 1/1999 | Yamaki et al. |
| 5,865,393 A | 2/1999 | Kreft et al. |
| 5,868,727 A | 2/1999 | Barr et al. |
| 5,876,027 A | 3/1999 | Fukui et al. |
| 5,876,792 A | 3/1999 | Caldwell |
| 5,879,500 A | 3/1999 | Herrin et al. |
| 5,897,291 A | 4/1999 | Gerwe et al. |
| 5,902,222 A | 5/1999 | Wessman |
| 5,902,431 A | 5/1999 | Wilkinson et al. |
| 5,904,675 A | 5/1999 | Laux et al. |
| 5,932,039 A | 8/1999 | Popp et al. |
| 5,935,367 A | 8/1999 | Hollenbeck |
| 5,938,193 A | 8/1999 | Bluemle et al. |
| 5,938,652 A | 8/1999 | Sauer |
| 5,964,390 A | 10/1999 | Borresen et al. |
| 5,964,970 A | 10/1999 | Woolwine et al. |
| 5,971,134 A | 10/1999 | Trefz et al. |
| 5,983,764 A | 11/1999 | Hillebrand |
| 6,009,781 A | 1/2000 | McNeil |
| 6,022,443 A | 2/2000 | Rajala et al. |
| 6,036,805 A | 3/2000 | McNichols |
| 6,043,836 A | 3/2000 | Kerr et al. |
| 6,050,517 A | 4/2000 | Dobrescu et al. |
| 6,074,110 A | 6/2000 | Verlinden et al. |
| 6,076,442 A | 6/2000 | Arterburn et al. |
| 6,080,909 A | 6/2000 | Osterdahl et al. |
| 6,098,249 A | 8/2000 | Toney et al. |
| 6,123,792 A | 9/2000 | Samida et al. |
| 6,138,436 A | 10/2000 | Malin et al. |
| 6,142,048 A | 11/2000 | Bradatsch et al. |
| 6,171,432 B1 | 1/2001 | Brisebois |
| 6,183,576 B1 | 2/2001 | Couillard et al. |
| 6,193,054 B1 | 2/2001 | Henson et al. |
| 6,193,702 B1 | 2/2001 | Spencer |
| 6,195,850 B1 | 3/2001 | Melbye |
| 6,196,147 B1 | 3/2001 | Burton et al. |
| 6,210,386 B1 | 4/2001 | Inoue |
| 6,212,859 B1 | 4/2001 | Bielik, Jr. et al. |
| 6,214,147 B1 | 4/2001 | Mortellite et al. |
| 6,217,274 B1 | 4/2001 | Svyatsky et al. |
| 6,250,048 B1 | 6/2001 | Linkiewicz |
| 6,264,639 B1 | 7/2001 | Sauer |
| 6,264,784 B1 | 7/2001 | Menard et al. |
| 6,276,421 B1 | 8/2001 | Valenti et al. |
| 6,276,587 B1 | 8/2001 | Borresen et al. |
| 6,280,373 B1 | 8/2001 | Lanvin |
| 6,284,081 B1 | 9/2001 | Vogt et al. |
| 6,287,409 B1 | 9/2001 | Stephany |
| 6,305,260 B1 | 10/2001 | Truttmann et al. |
| 6,306,122 B1 | 10/2001 | Narawa et al. |
| 6,309,336 B1 | 10/2001 | Muessig et al. |
| 6,312,420 B1 | 11/2001 | Sasaki et al. |
| 6,314,333 B1 | 11/2001 | Rajala et al. |
| 6,315,022 B1 | 11/2001 | Herrin et al. |
| 6,319,347 B1 | 11/2001 | Rajala |
| 6,336,921 B1 | 1/2002 | Kato et al. |
| 6,336,922 B1 | 1/2002 | VanGompel et al. |
| 6,336,923 B1 | 1/2002 | Fujioka et al. |
| 6,358,350 B1 | 3/2002 | Glaug et al. |
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturino et al. |
| 6,425,430 B1 | 7/2002 | Ward et al. |
| 6,431,038 B2 | 8/2002 | Couturier |
| 6,440,246 B1 | 8/2002 | Vogt et al. |
| 6,443,389 B1 | 9/2002 | Palone |
| 6,446,795 B1 | 9/2002 | Allen et al. |
| 6,473,669 B2 | 10/2002 | Rajala et al. |
| 6,475,325 B1 | 11/2002 | Parrish et al. |
| 6,478,786 B1 | 11/2002 | Glaug et al. |
| 6,482,278 B1 | 11/2002 | McCabe et al. |
| 6,494,244 B2 | 12/2002 | Parrish et al. |
| 6,514,233 B1 | 2/2003 | Glaug |
| 6,521,320 B2 | 2/2003 | McCabe et al. |
| 6,523,595 B1 | 2/2003 | Milner et al. |
| 6,524,423 B1 | 2/2003 | Hilt et al. |
| 6,533,879 B2 | 3/2003 | Quereshi et al. |
| 6,540,857 B1 | 4/2003 | Coenen et al. |
| 6,547,909 B1 | 4/2003 | Butterworth |
| 6,550,517 B1 | 4/2003 | Hilt et al. |
| 6,551,228 B1 | 4/2003 | Richards |
| 6,551,430 B1 | 4/2003 | Glaug et al. |
| 6,554,815 B1 | 4/2003 | Umebayashi |
| 6,557,466 B2 | 5/2003 | Codde et al. |
| 6,569,275 B1 | 5/2003 | Popp et al. |
| 6,572,520 B2 | 6/2003 | Blumle |
| 6,581,517 B1 | 6/2003 | Becker et al. |
| 6,585,841 B1 | 7/2003 | Popp et al. |
| 6,589,149 B1 | 7/2003 | VanEperen et al. |
| 6,596,107 B2 | 7/2003 | Stopher |
| 6,596,108 B2 | 7/2003 | McCabe |
| 6,605,172 B1 | 8/2003 | Anderson et al. |
| 6,605,173 B1 | 8/2003 | Glaug et al. |
| 6,620,276 B1 | 9/2003 | Kuntze et al. |
| 6,632,209 B1 | 10/2003 | Chmielewski |
| 6,634,269 B2 | 10/2003 | Eckstein et al. |
| 6,637,583 B1 | 10/2003 | Anderson |
| 6,648,122 B1 | 11/2003 | Hirsch et al. |
| 6,649,010 B2 | 11/2003 | Parrish et al. |
| 6,656,309 B1 | 12/2003 | Parker et al. |

(56) References Cited

U.S. PATENT DOCUMENTS

| | | |
|---|---|---|
| 6,659,150 B1 | 12/2003 | Perkins et al. |
| 6,659,991 B2 | 12/2003 | Suckane |
| 6,675,552 B2 | 1/2004 | Kunz et al. |
| 6,682,626 B2 | 1/2004 | Mlinar et al. |
| 6,684,925 B2 | 2/2004 | Nagate et al. |
| 6,685,130 B2 | 2/2004 | Stauber et al. |
| 6,722,494 B2 | 4/2004 | Nakakado |
| 6,730,189 B1 | 5/2004 | Franzmann |
| 6,743,324 B2 | 6/2004 | Hargett et al. |
| 6,750,466 B2 | 6/2004 | Guha et al. |
| 6,758,109 B2 | 7/2004 | Nakakado |
| 6,766,817 B2 | 7/2004 | da Silva |
| 6,779,426 B1 | 8/2004 | Holliday |
| 6,808,582 B2 | 10/2004 | Popp et al. |
| D497,991 S | 11/2004 | Otsubo et al. |
| 6,811,019 B2 | 11/2004 | Christian et al. |
| 6,811,642 B2 | 11/2004 | Ochi |
| 6,814,217 B2 | 11/2004 | Blumenthal et al. |
| 6,820,671 B2 | 11/2004 | Calvert |
| 6,823,981 B2 | 11/2004 | Ogle et al. |
| 6,837,840 B2 | 1/2005 | Yonekawa et al. |
| 6,840,616 B2 | 1/2005 | Summers |
| 6,852,186 B1 | 2/2005 | Matsuda et al. |
| 6,869,494 B2 | 3/2005 | Roessler et al. |
| 6,875,202 B2 | 4/2005 | Kumasaka et al. |
| 6,884,310 B2 | 4/2005 | Roessler et al. |
| 6,893,528 B2 | 5/2005 | Middelstadt et al. |
| 6,913,664 B2 | 7/2005 | Umebayashi et al. |
| 6,913,718 B2 | 7/2005 | Ducker |
| 6,918,404 B2 | 7/2005 | Dias da Silva |
| 6,976,521 B2 | 12/2005 | Mlinar |
| 6,978,486 B2 | 12/2005 | Zhou et al. |
| 6,978,964 B2 | 12/2005 | Beccari |
| 7,017,321 B2 | 3/2006 | Salvoni |
| 7,017,820 B1 | 3/2006 | Brunner |
| 7,045,031 B2 | 5/2006 | Popp et al. |
| 7,047,852 B2 | 5/2006 | Franklin et al. |
| 7,048,725 B2 | 5/2006 | Kling et al. |
| 7,066,586 B2 | 6/2006 | da Silva |
| 7,069,970 B2 | 7/2006 | Tomsovic et al. |
| 7,077,393 B2 | 7/2006 | Ishida |
| 7,130,710 B2 | 10/2006 | Popp et al. |
| 7,137,971 B2 | 11/2006 | Tanzer |
| 7,172,666 B2 | 2/2007 | Groves et al. |
| 7,175,584 B2 | 2/2007 | Maxton et al. |
| 7,195,684 B2 | 3/2007 | Satoh |
| 7,201,345 B2 | 4/2007 | Werner |
| 7,204,682 B2 | 4/2007 | Venturino et al. |
| 7,214,174 B2 | 5/2007 | Allen et al. |
| 7,214,287 B2 | 5/2007 | Shiomi |
| 7,220,335 B2 | 5/2007 | Van Gompel et al. |
| 7,247,219 B2 | 7/2007 | O'Dowd |
| 7,252,730 B2 | 8/2007 | Hoffman et al. |
| 7,264,686 B2 | 9/2007 | Thorson et al. |
| 7,303,708 B2 | 12/2007 | Andrews et al. |
| 7,326,311 B2 | 2/2008 | Krueger et al. |
| 7,332,459 B2 | 2/2008 | Collins et al. |
| 7,374,627 B2 | 5/2008 | McCabe |
| 7,380,213 B2 | 5/2008 | Pokorny et al. |
| 7,398,870 B2 | 7/2008 | McCabe |
| 7,399,266 B2 | 7/2008 | Aiolfi et al. |
| 7,449,084 B2 | 11/2008 | Nakakado |
| 7,452,436 B2 | 11/2008 | Andrews |
| 7,500,941 B2 | 3/2009 | Coe et al. |
| 7,533,709 B2 | 5/2009 | Meyer |
| 7,537,215 B2 | 5/2009 | Beaudoin et al. |
| 7,569,007 B2 | 8/2009 | Thoma |
| 7,587,966 B2 | 9/2009 | Nakakado et al. |
| 7,618,513 B2 | 11/2009 | Meyer |
| 7,638,014 B2 | 12/2009 | Coose et al. |
| 7,640,962 B2 | 1/2010 | Meyer et al. |
| 7,695,464 B2 | 4/2010 | Fletcher et al. |
| 7,703,599 B2 | 4/2010 | Meyer |
| 7,708,849 B2 | 5/2010 | McCabe |
| 7,770,712 B2 | 8/2010 | McCabe |
| 7,771,407 B2 | 8/2010 | Umebayashi |
| 7,780,052 B2 | 8/2010 | McCabe |
| 7,793,772 B2 | 9/2010 | Schafer |
| 7,811,403 B2 | 10/2010 | Andrews |
| 7,861,756 B2 | 1/2011 | Jenquin et al. |
| 7,871,400 B2 | 1/2011 | Sablone et al. |
| 7,909,956 B2 | 3/2011 | Coose et al. |
| 7,922,983 B2 | 4/2011 | Prokash et al. |
| 7,935,296 B2 | 5/2011 | Koele et al. |
| 7,975,584 B2 | 7/2011 | McCabe |
| 7,987,964 B2 | 8/2011 | McCabe |
| 8,007,484 B2 | 8/2011 | McCabe et al. |
| 8,007,623 B2 | 8/2011 | Andrews |
| 8,011,493 B2 | 9/2011 | Giuliani et al. |
| 8,016,972 B2 | 9/2011 | Andrews et al. |
| 8,025,652 B2 | 9/2011 | Hornung et al. |
| 8,062,279 B2 | 11/2011 | Miyamoto |
| 8,062,459 B2 | 11/2011 | Nakakado et al. |
| 8,100,173 B2 | 1/2012 | Hornung et al. |
| 8,172,977 B2 | 5/2012 | Andrews et al. |
| 8,176,573 B2 | 5/2012 | Popp et al. |
| 8,178,035 B2 | 5/2012 | Edvardsson et al. |
| 8,182,624 B2 | 5/2012 | Handziak |
| 8,182,735 B2 | 5/2012 | Edvardsson |
| 8,182,736 B2 | 5/2012 | Edvardsson |
| 8,257,237 B2 | 9/2012 | Burns, Jr. et al. |
| 8,273,003 B2 | 9/2012 | Umebayashi et al. |
| 8,293,056 B2 | 10/2012 | McCabe |
| 8,295,552 B2 | 10/2012 | Mirtich et al. |
| 8,381,489 B2 | 2/2013 | Freshwater et al. |
| 8,398,793 B2 | 3/2013 | Andrews et al. |
| 8,417,374 B2 | 4/2013 | Meyer et al. |
| 8,439,814 B2 | 5/2013 | Piantoni et al. |
| 8,460,495 B2 | 6/2013 | McCabe |
| 8,485,956 B2 | 7/2013 | Burns, Jr. et al. |
| 8,512,496 B2 | 8/2013 | Makimura |
| 8,607,959 B2 * | 12/2013 | Papsdorf et al. .......... 198/377.04 |
| 8,656,817 B2 | 2/2014 | Fritz et al. |
| 8,663,411 B2 | 3/2014 | McCabe |
| 8,673,098 B2 | 3/2014 | McCabe |
| 8,794,115 B2 * | 8/2014 | McCabe ........................ 83/23 |
| 2001/0012813 A1 | 8/2001 | Bluemle |
| 2001/0017181 A1 | 8/2001 | Otruba et al. |
| 2001/0035332 A1 | 11/2001 | Zeitler |
| 2001/0042591 A1 | 11/2001 | Milner et al. |
| 2002/0040630 A1 | 4/2002 | Piazza |
| 2002/0046802 A1 | 4/2002 | Tachibana et al. |
| 2002/0059013 A1 | 5/2002 | Rajala et al. |
| 2002/0084568 A1 | 7/2002 | Codde et al. |
| 2002/0096241 A1 | 7/2002 | Instance |
| 2002/0125105 A1 | 9/2002 | Nakakado |
| 2002/0162776 A1 | 11/2002 | Hergeth |
| 2003/0000620 A1 | 1/2003 | Herrin et al. |
| 2003/0015209 A1 | 1/2003 | Gingras et al. |
| 2003/0051802 A1 | 3/2003 | Hargett et al. |
| 2003/0052148 A1 | 3/2003 | Rajala et al. |
| 2003/0066585 A1 | 4/2003 | McCabe |
| 2003/0083638 A1 | 5/2003 | Molee |
| 2003/0084984 A1 | 5/2003 | Glaug et al. |
| 2003/0089447 A1 | 5/2003 | Molee et al. |
| 2003/0115660 A1 | 6/2003 | Hopkins |
| 2003/0121244 A1 | 7/2003 | Abba et al. |
| 2003/0121614 A1 | 7/2003 | Tabor et al. |
| 2003/0135189 A1 | 7/2003 | Umebayashi |
| 2003/0150551 A1 | 8/2003 | Baker |
| 2003/0226862 A1 | 12/2003 | Vogt et al. |
| 2004/0007328 A1 | 1/2004 | Popp et al. |
| 2004/0016500 A1 | 1/2004 | Tachibana et al. |
| 2004/0044325 A1 | 3/2004 | Corneliusson |
| 2004/0073187 A1 | 4/2004 | Karami |
| 2004/0084468 A1 | 5/2004 | Kelbert et al. |
| 2004/0087425 A1 | 5/2004 | Ng et al. |
| 2004/0098791 A1 | 5/2004 | Faulks |
| 2004/0112517 A1 | 6/2004 | Groves et al. |
| 2004/0122413 A1 | 6/2004 | Roessler et al. |
| 2004/0157041 A1 | 8/2004 | Leboeuf et al. |
| 2004/0164482 A1 | 8/2004 | Edinger |
| 2004/0167493 A1 | 8/2004 | Jarpenberg et al. |
| 2004/0177737 A1 | 9/2004 | Adami |

(56) References Cited

U.S. PATENT DOCUMENTS

| | | |
|---|---|---|
| 2004/0182213 A1 | 9/2004 | Wagner et al. |
| 2004/0182497 A1 | 9/2004 | Lowrey |
| 2004/0216830 A1 | 11/2004 | Van Eperen |
| 2004/0228709 A1 | 11/2004 | Ueda |
| 2005/0000628 A1 | 1/2005 | Norrby |
| 2005/0022476 A1 | 2/2005 | Hamer |
| 2005/0026760 A1 | 2/2005 | Yamamoto et al. |
| 2005/0056678 A1 | 3/2005 | Nomura et al. |
| 2005/0077418 A1 | 4/2005 | Werner et al. |
| 2005/0101929 A1 | 5/2005 | Waksmundzki et al. |
| 2005/0139713 A1 | 6/2005 | Weber et al. |
| 2005/0196538 A1 | 9/2005 | Sommer et al. |
| 2005/0230056 A1 | 10/2005 | Meyer et al. |
| 2005/0230449 A1 | 10/2005 | Meyer et al. |
| 2005/0233881 A1 | 10/2005 | Meyer |
| 2005/0234412 A1 | 10/2005 | Andrews et al. |
| 2005/0257881 A1 | 11/2005 | Coose et al. |
| 2005/0275148 A1 | 12/2005 | Beaudoin et al. |
| 2006/0011030 A1 | 1/2006 | Wagner et al. |
| 2006/0021300 A1 | 2/2006 | Tada et al. |
| 2006/0099055 A1 | 5/2006 | Stefani |
| 2006/0137298 A1 | 6/2006 | Oshita et al. |
| 2006/0199718 A1 | 9/2006 | Thoma |
| 2006/0201619 A1 | 9/2006 | Andrews |
| 2006/0224137 A1 | 10/2006 | McCabe et al. |
| 2006/0265867 A1 | 11/2006 | Schaap |
| 2006/0266465 A1 | 11/2006 | Meyer |
| 2007/0074953 A1 | 4/2007 | McCabe |
| 2007/0131343 A1 | 6/2007 | Nordang |
| 2007/0131817 A1 | 6/2007 | Fromm et al. |
| 2007/0140817 A1 | 6/2007 | Hansl |
| 2008/0041206 A1 | 2/2008 | Mergola et al. |
| 2008/0125738 A1 | 5/2008 | Tsuji et al. |
| 2008/0208152 A1 | 8/2008 | Eckstein et al. |
| 2008/0210067 A1 | 9/2008 | Schlinz et al. |
| 2008/0223537 A1 | 9/2008 | Wiedmann |
| 2008/0281286 A1 | 11/2008 | Petersen |
| 2008/0287898 A1 | 11/2008 | Guzman Reyes et al. |
| 2009/0020211 A1 | 1/2009 | Andrews et al. |
| 2009/0126864 A1 | 5/2009 | Tachibana et al. |
| 2009/0198205 A1 | 8/2009 | Malowaniec et al. |
| 2009/0212468 A1 | 8/2009 | Edvardsson et al. |
| 2010/0078119 A1 | 4/2010 | Yamamoto |
| 2010/0078120 A1 | 4/2010 | Otsubo |
| 2010/0078127 A1 | 4/2010 | Yamamoto |
| 2010/0193135 A1 | 8/2010 | Eckstein et al. |
| 2010/0193138 A1 | 8/2010 | Eckstein |
| 2010/0193155 A1 | 8/2010 | Nakatani |
| 2010/0249737 A1 | 9/2010 | Ito et al. |
| 2011/0003673 A1 | 1/2011 | Piantoni et al. |
| 2011/0033270 A1 | 2/2011 | Toncelli |
| 2011/0106042 A1 | 5/2011 | Sablone et al. |
| 2012/0079926 A1 | 4/2012 | Long et al. |
| 2012/0123377 A1 | 5/2012 | Back |
| 2012/0172828 A1 | 7/2012 | Koenig et al. |
| 2012/0270715 A1 | 10/2012 | Motegi et al. |
| 2012/0285306 A1 | 11/2012 | Weibelt |
| 2012/0310193 A1 | 12/2012 | Ostertag |
| 2012/0312463 A1 | 12/2012 | Ogasawara et al. |
| 2013/0066613 A1 | 3/2013 | Russell |
| 2013/0079741 A1 | 3/2013 | Nakashita et al. |
| 2013/0239765 A1 | 9/2013 | McCabe et al. |
| 2014/0155855 A1 | 6/2014 | Romzek et al. |

FOREIGN PATENT DOCUMENTS

| | | |
|---|---|---|
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2330679 | 9/1999 |
| CA | 2404154 | 10/2001 |
| CA | 2541194 | 10/2006 |
| CA | 2559517 | 4/2007 |
| CA | 2337700 | 8/2008 |
| CA | 2407867 | 6/2010 |
| CA | 2699136 | 10/2010 |
| CA | 142627 | 6/2013 |
| CA | 2600432 | 7/2013 |
| CA | 2573445 | 3/2014 |
| CA | 2547464 | 4/2014 |
| CA | 155189 | 12/2014 |
| CN | 202105105 | 1/2012 |
| DE | 60123502 | 10/2006 |
| DE | 60216550 | 12/2006 |
| DE | 102005035544 | 2/2007 |
| DE | 1020060472-80 | 4/2007 |
| DE | 102005048868 | 4/2007 |
| DE | 102007063209 | 6/2009 |
| EP | 0044206 | 1/1982 |
| EP | 0048011 | 3/1982 |
| EP | 0089106 | 9/1983 |
| EP | 0099732 | 2/1984 |
| EP | 0206208 | 12/1986 |
| EP | 0304140 | 2/1989 |
| EP | 0411287 | 2/1991 |
| EP | 0439897 | 8/1991 |
| EP | 0455231 A1 | 11/1991 |
| EP | 510251 | 10/1992 |
| EP | 0589859 | 3/1994 |
| EP | 0676352 | 4/1995 |
| EP | 0652175 A1 | 5/1995 |
| EP | 0811473 | 12/1997 |
| EP | 0812789 A2 | 12/1997 |
| EP | 0901780 | 3/1999 |
| EP | 0990588 | 4/2000 |
| EP | 1132325 A2 | 9/2001 |
| EP | 1035818 | 4/2002 |
| EP | 1199057 | 4/2002 |
| EP | 1366734 | 12/2003 |
| EP | 1393701 | 3/2004 |
| EP | 1415628 | 5/2004 |
| EP | 1433731 | 6/2004 |
| EP | 1571249 | 9/2005 |
| EP | 1619008 | 1/2006 |
| EP | 1707168 A2 | 10/2006 |
| EP | 1726414 | 11/2006 |
| EP | 1302424 | 12/2006 |
| EP | 1801045 | 6/2007 |
| EP | 1870067 | 12/2007 |
| EP | 1941853 | 7/2008 |
| EP | 1961403 | 8/2008 |
| EP | 1994919 | 11/2008 |
| EP | 2180864 | 11/2008 |
| EP | 2211812 | 11/2008 |
| EP | 2103427 | 9/2009 |
| EP | 2233116 | 9/2010 |
| EP | 2238955 | 10/2010 |
| EP | 1175880 | 5/2012 |
| EP | 2508156 A1 | 10/2012 |
| EP | 1868821 | 1/2013 |
| EP | 2036522 | 3/2013 |
| EP | 1272347 | 4/2013 |
| EP | 2032338 | 8/2013 |
| EP | 2659869 A1 | 11/2013 |
| EP | 2332505 | 12/2013 |
| EP | 2412348 | 3/2014 |
| EP | 2829257 A1 | 1/2015 |
| ES | 509706 | 11/1982 |
| ES | 520559 | 12/1983 |
| ES | 296211 | 12/1987 |
| ES | 2310447 | 7/2009 |
| ES | 2311349 | 9/2009 |
| FR | 2177355 | 11/1973 |
| FR | 2255961 | 7/1975 |
| FR | 1132325 | 10/2006 |

(56) References Cited

FOREIGN PATENT DOCUMENTS

| | | |
|---|---|---|
| FR | 2891811 | 4/2007 |
| GB | 191101501 A | 0/1912 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 1467470 | 3/1977 |
| GB | 2045298 | 10/1980 |
| GB | 2115775 | 9/1983 |
| GB | 2288316 | 10/1995 |
| IT | 1374910 | 5/2010 |
| IT | 1374911 | 5/2010 |
| JP | 428364 | 1/1992 |
| JP | 542180 | 2/1993 |
| JP | 576566 | 3/1993 |
| JP | 626160 | 2/1994 |
| JP | 626161 | 2/1994 |
| JP | 6197925 A | 7/1994 |
| JP | 9299398 | 11/1997 |
| JP | 10035621 | 2/1998 |
| JP | 10-277091 A | 10/1998 |
| JP | 2008-161300 | 7/2008 |
| SE | 0602047 | 5/2007 |
| SE | 529295 | 6/2007 |
| SE | 532059 | 10/2009 |
| WO | WO93/15248 | 8/1993 |
| WO | WO9403301 | 2/1994 |
| WO | WO97/23398 | 7/1997 |
| WO | WO9732552 | 9/1997 |
| WO | WO9747265 | 12/1997 |
| WO | WO9747810 | 12/1997 |
| WO | WO9821134 | 5/1998 |
| WO | WO98/55298 | 12/1998 |
| WO | WO9907319 | 2/1999 |
| WO | WO9913813 A1 | 3/1999 |
| WO | WO9932385 | 7/1999 |
| WO | WO9965437 | 12/1999 |
| WO | WO 01/02277 A2 | 1/2001 |
| WO | WO0143682 | 6/2001 |
| WO | WO0172237 A2 | 10/2001 |
| WO | WO03/031177 | 4/2003 |
| WO | WO2004007329 | 1/2004 |
| WO | WO2005075163 | 8/2005 |
| WO | WO2006038946 | 4/2006 |
| WO | WO2007029115 | 3/2007 |
| WO | WO2007039800 | 4/2007 |
| WO | WO2007126347 | 11/2007 |
| WO | WO2008001209 | 1/2008 |
| WO | WO2008/015594 | 2/2008 |
| WO | WO2008037281 | 4/2008 |
| WO | WO2008/123348 | 10/2008 |
| WO | WO2008155618 | 12/2008 |
| WO | WO2009/065497 | 3/2009 |
| WO | WO2009/065500 | 3/2009 |
| WO | WO2010028786 | 3/2010 |
| WO | WO2011101773 | 8/2011 |
| WO | WO2012/123813 A1 | 9/2012 |
| WO | WO 2014/021897 | 2/2014 |

\* cited by examiner

VENTILATED VACUUM COMMUTATION STRUCTURES

RELATED APPLICATION

This application claims the benefit of U.S. Provisional Patent Application Ser. No. 61/857,905, filed 24 Jul. 2013.

BACKGROUND OF THE INVENTION

This invention related to an apparatus for transferring articles such as absorbent pads in the manufacture of disposable absorbent articles such as diapers, incontinence control garments or female sanitary pads as they advance along a production line.

In the production and manufacture of disposable products such as sanitary napkins or pants-type diapers, it frequently becomes necessary to manufacture a component of the product in one orientation, and then to rotate that component part 90° so that it is suitably oriented for use in another step in the production process. Various devices have been developed for this purpose and are known to those experienced in the industry. Examples of such apparatus are those described in U.S. Pat. Nos. 4,726,876, 4,880,102, and 5,025,910, the disclosures of which are incorporated herein by reference.

As discussed above, a typical article to be reoriented by the apparatus of this invention is an absorbent pad. Because absorbent pads are typically comprised of several webs, an absorbent core and several elastic members, there is a tendency of these assemblies to contract and become distorted during transfer operations which greatly complicates handling of the pad during further processing. Control of the pad is important.

Other components of disposable products including ears, or extension panels, require transportation and deposition by a vacuum puck. For instance, in U.S. Pat. No. 8,016,972, assigned to the same assignee as the present invention, ear webs are severed into individual ears, and rotated while held by a vacuum puck, to be applied to a traveling web such as a chassis web.

An ear is a component of a diaper that is grasped and pulled around the waist of a wearer. Typically, ears are secured to the diaper at a first end, and a second free end is typically equipped with securing means, such as a pressure sensitive adhesive, or hook and loop material. As a user grasps an ear and pulls the ear, elasticity provided about the waist region of the diaper allows the free end to be snugly pulled about the waist of a wearer, and coupled to the diaper. Ears can be rectangular or made of irregular shapes.

Typical vacuum pucks used in the prior art have rows of vacuum holes which are fed by cross-drilled ports, each being exposed to the source of vacuum by commutations, as the ports move into a zone of negative pressure in a stationary manifold. Such a configuration serves to apply vacuum sequentially to each successive row of holes. At high speeds, it has been found that air entering the vacuum ports is drawn across an article carrying face of the puck, and the air drawn into the ports can adversely impact control over the discrete components by causing misalignment, folding or other loss of total control.

SUMMARY OF THE INVENTION

The apparatus of the present invention is a ventilated puck for discrete items such as portions of a disposable diaper during the manufacturing process.

The puck picks up an article from a first conveying means, and deposits the article onto another conveying means.

The puck is ventilated in order to provide for minimization of disruptive air flow. Instead of air being drawn from edges and across an article carrying face of the puck, air is able to approach vacuum ports from underneath the carrying face of the puck, proximally to the vacuum ports.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
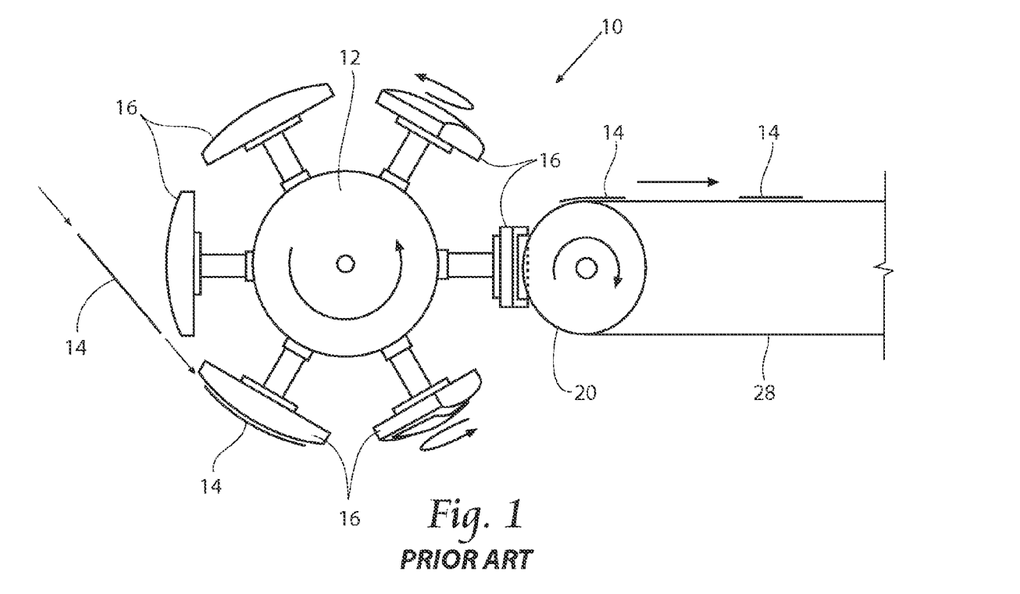
FIG. 1 is a fragmentary side elevation view, shown in diagrammatic form, of a pad transferring assembly including a puck of the prior art.

Referring more particularly to the drawings, there is seen in FIG. 1 an apparatus 10 carrying pucks, or transfer heads 16, of the prior art. The apparatus 10 is adapted to receive a series of articles 14 from an upstream conveyor or vacuum drum (not shown) onto a pad turning device 12 which includes a plurality of radially extending transfer heads 16.

The location where articles 14 are received from the upstream point onto the pucks 16 is known as the pick up point. The location where articles 14 are deposited from the pucks 16 to a downstream drum or conveyor 20 is known as the lay down point.

The pad turning device 12 may be, for example, a rotary pad turner of the type more fully described in U.S. Pat. No. 5,025,910 which is incorporated herein by reference. The articles 14 can be of any type, but are typically absorbent pads, ears, or extension panels. During manufacturing, each of these requires transportation and deposition by a vacuum puck, and sometimes rotation or reorientation of a discrete piece is also desirable prior to deposition onto another portion of an absorbent article. Such pad turning devices 12 are especially needed and are suited for use in connection with the manufacture and packaging of sanitary napkins as well as absorbent pads which are used in the assembly of disposable garments such as adult incontinence garments or children's training pants.

Also seen in FIG. 1, articles 14 are successively and individually picked-up by the transfer heads 16 of the pad transfer device 12. In the illustrated embodiment, the articles 14 are picked up from a vacuum drum (not shown). Various conventional conveying and direction changing devices such as rollers may be employed in the feeding of the web and do not form a part of this invention.

After the articles 14 have been rotated 90 degrees, they are deposited at the lay down point onto a second vacuum source, for example a drum 20. A conveyor 28 or the like transport the articles 14 for further processing or to a packaging device, as required by a particular application. Alternatively, the deposition point can be for instance a coupling point for an ear or an extension panel onto a chassis web, such as shown and described in U.S. Pat. No. 8,016,972, incorporated herein by reference.

Figure 2:
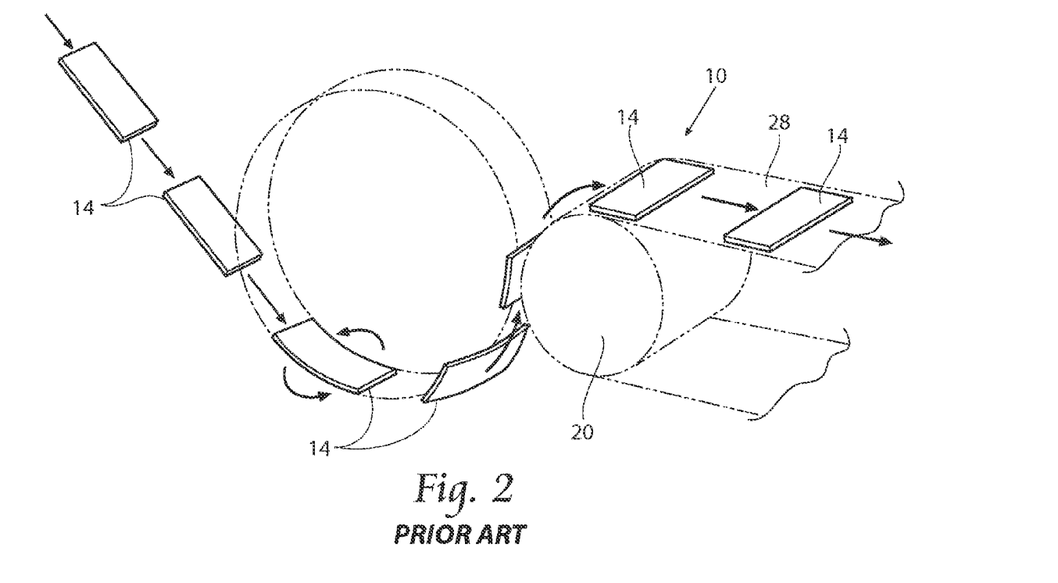
FIG. 2 is a perspective fragmentary, diagrammatic view, showing related apparatus by means of phantom lines and illustrating the path of movement of discrete pieces such pads moving in accordance with the invention.

Referring to FIG. 2, there is seen a diagrammatic depiction of the travel path of the web 22 and the resultant pads 14 which are formed therefrom. In this depiction the various apparatus have been eliminated but are partially illustrated by means of phantom lines.

As can be seen, the article is rotated 90° from the pick up point to the lay down point, and is also stretched during this time it spends on the puck 16. In some instance however, it is not necessary to rotate the article between pick up and lay down, depending on the design of the article being produced or the manufacturing technique used.

Figure 3:
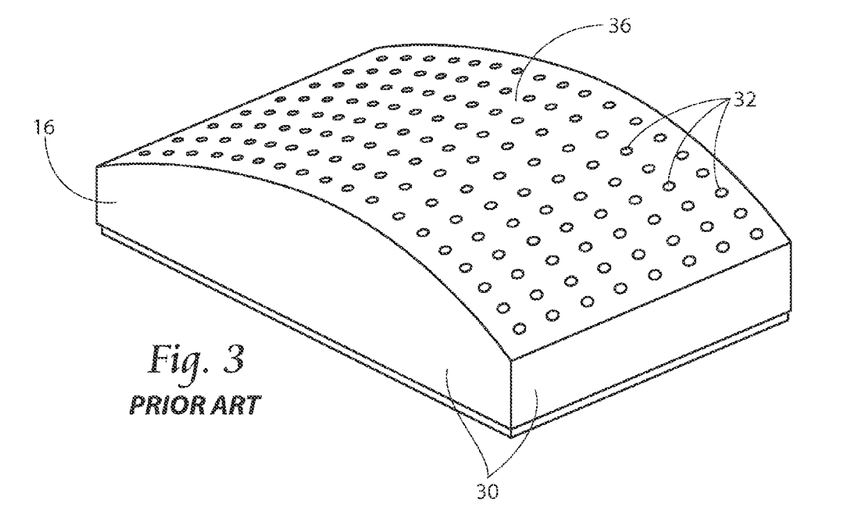
FIG. 3 is a perspective view of a non-ventilated puck of the prior art.

As shown in FIG. 3, a perspective view of an embodiment of a prior art puck 16 prior art is shown. At high speeds, it has been found that air entering vacuum ports 32 is drawn across an article carrying face 36 of the puck 16, and the air drawn into the ports 32 can adversely impact control over the discrete components by causing misalignment, folding or other loss of total control.

Figures 4, 5:
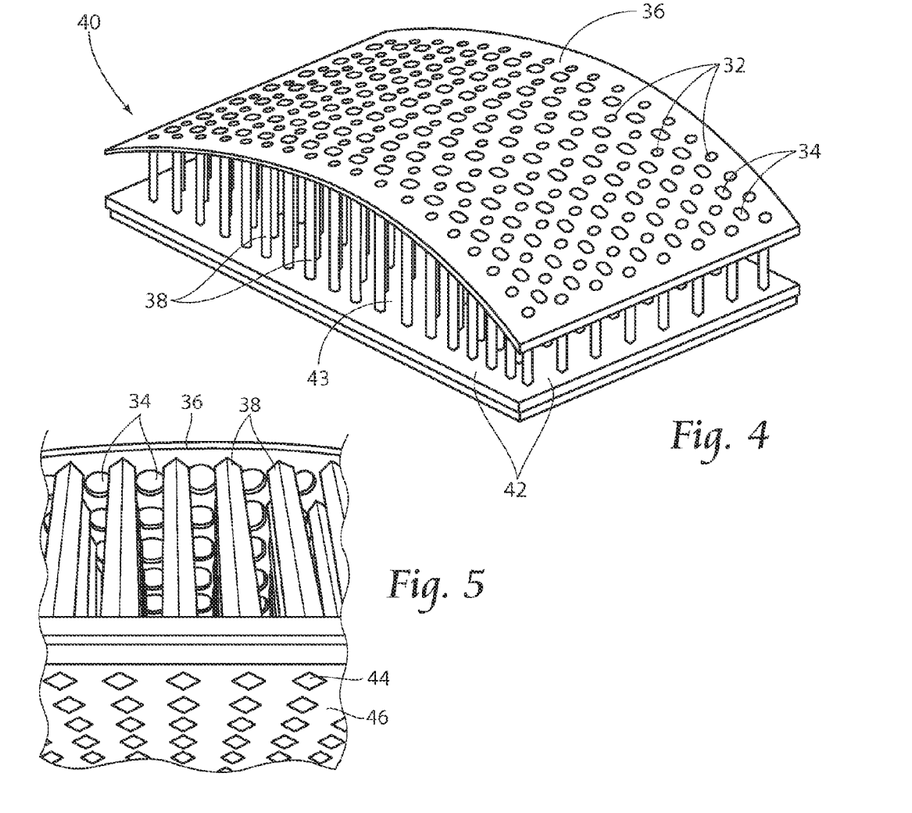
FIG. 4 is a perspective view of a ventilated puck of the present invention.
FIG. 5 is a bottom perspective view of an embodiment of a ventilated puck of the present invention.

Referring now to FIG. 4, a perspective view of one embodiment of a ventilated puck 40 of the present invention is shown. Air is drawn into commutation ports 32 by commutation pipes 38. The pipes 38 carry a preferably radially shaped vented article carrying structure 36, although flat pucks can also be used. A plurality of air supplying vents 34 are situated about vacuum commutation ports 32. Air supply vents 34 receive air drawn through sides 43 of the ventilated puck 40, and drawn through the air surrounding the commutation pipes 38. The ventilated puck 40 preferably lacks solid sidewalls 30 as shown in prior art pucks such as FIG. 3, allowing the ingress of air through the void sides 42 into the interior of the puck 40, as well as through air supplying vents 34 not overlain by a discrete piece of material. The air enters the interior vacuum ports 44 from the underside of article carrying structure 36, and the air is drawn into proximally situated vacuum ports 32.

The commutation pipes 38 are rigid enough to support the vented article carrying structure, and rigid enough to withstand collapse due to applied vacuum. And although the commutation pipes 38 are depicted as narrow square tubular in shape leading to the small and circular vacuum commutation ports 32, the commutation pipes 38, the air supplying vents 34, and the vacuum commutation ports 32 can take different cross-sectional shapes, such as star shaped, circular, oval, rectangular, etc.

A pattern of vacuum ports 32 is provided on the surface of article carrying structure 36 through which the internal vacuum acts to draw the pads 14 towards the surface. It is clear that this technology can be applied to the transfer and placement of many different types of articles in the disposable goods industry and other industries as well.

Metal laser sintering is a good way to make the products of the present invention.

Referring now to FIG. 5, vacuum is drawn through interior vacuum ports 44 of commutation pipes 38 in a manner such as shown in U.S. Pat. No. 7,770,712, which is incorporated by reference. Commutation pipes 38 extend between and are coupled to a vacuum port plate 46 and the article carrying structure 36. Together, the commutation pipes 38, vacuum port plate 46 and the article carrying structure 36 of the puck 16 are rotated and supplied with vacuum as previously described.

Figures 6, 7, 8, 9:
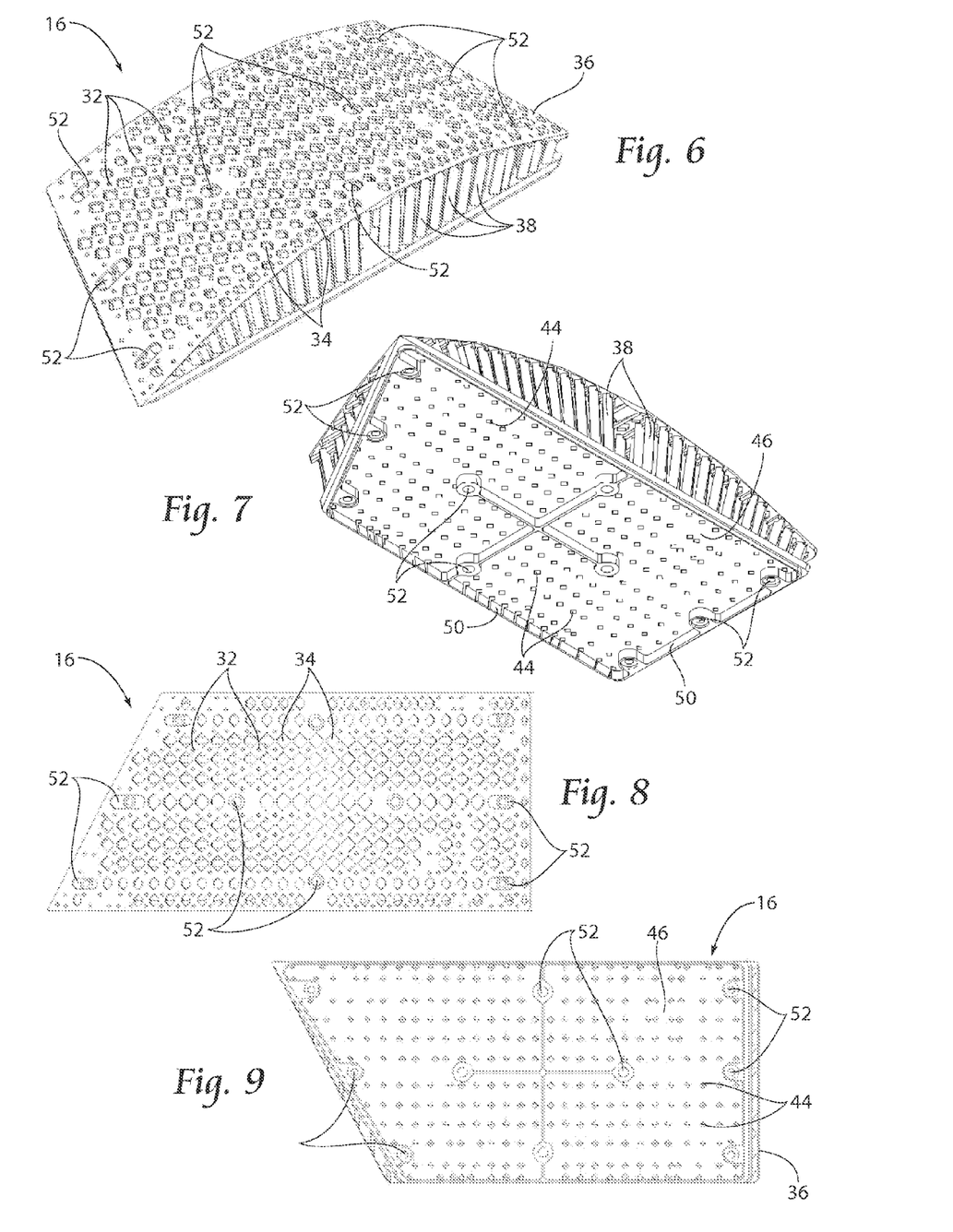
FIG. 6 is a top perspective view of ventilated puck of the present invention.
FIG. 7 is a bottom perspective view of a ventilated puck of the present invention.
FIG. 8 is a to view of a ventilated puck of the present invention.
FIG. 9 is a bottom view of a ventilated puck of the present invention.
Figure 10:
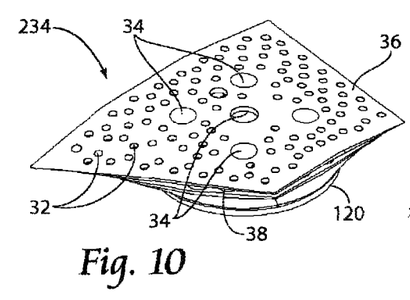
FIG. 10 is a perspective view of an alternative embodiment of a ventilated puck.
Figure 11:
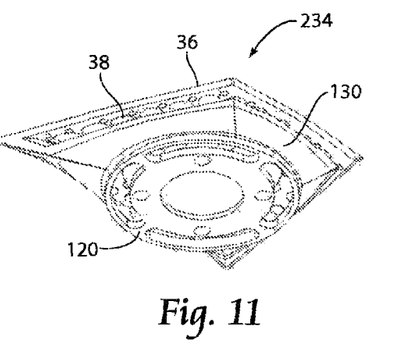
FIG. 11 is a bottom perspective view of the puck shown in FIG. 10.
Figure 12:
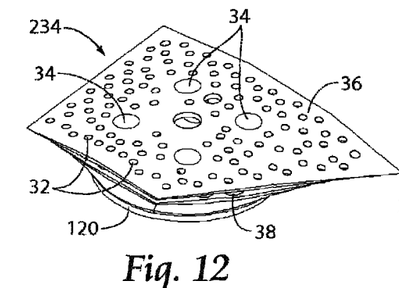
FIG. 12 is a perspective view of an additional alternative embodiment of a ventilated puck.
Figure 13:
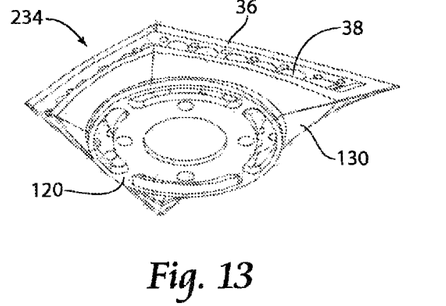
FIG. 13 is a bottom perspective view of the puck shown in FIG. 12.

Referring now to FIG. 6, a top perspective view of the article carrying structure 36 of the puck 16 is shown. The article carrying structure, as previously described, has a plurality of circular vacuum commutation ports 32 and air supplying vents 34, both of which can vary in shape, size, or distribution. A plurality of clearance holes 52 for mounting the puck 16 are shown. As shown on FIG. 7, corresponding clearance holes 52 on the vacuum port plate 46 for receiving a coupling means (such as a screw) through both sets of clearing holes 52, and are used to couple the puck 16 to a receiving surface/apparatus (not shown). Sidewalls 50 of the vacuum port plate 46, together with a vacuum manifold (not shown), provide vacuum to the regions defined by the sidewalls 50. FIGS. 8 and 9 show a top and a bottom view of a ventilated puck 16 of the present invention.

Figure 14:
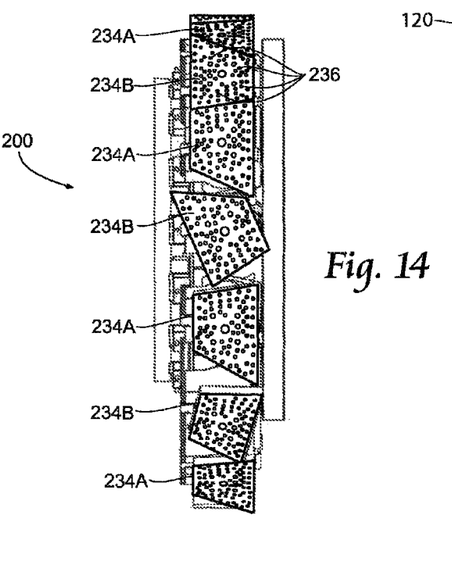
FIG. 14 is a front view of a rotating body carrying rotating ventilated pucks.

In the embodiment depicted in FIGS. 6-9, a plurality of side and top ventilated pucks 16 can be joined together on a rotting device (e.g., FIG. 14) such that the article carrying structures 36 of the pucks 16 present a radius around the rotating device. In a preferred embodiment, the article carrying structures 36 of the pucks 16 are trapezoidal in top view, and if a flat vacuum port plate 46 is used, the commutation pipes 38 will be of varying lengths to accommodate the variable distance between the flat port plate 46 and curved article carrying structure 36. Because the article carrying structures 36 are curved, the portion of the commutation pipes 38 that meet the article carrying structures 36 are also curved. The portion of the commutation pipes 38 that meet the flat port plates 46 are flat.

Referring now to FIGS. 10-13, an alternative embodiment of a ventilated puck 234 is shown. As can be seen from FIG. 14, two types of pucks are provided, non-rotating pucks 234A and rotating pucks 234B. The non-rotating pucks 234A carry ears (not shown) that do not require rotation, and the rotating pucks 234B carry ears requiring rotation. As the ear turner assemblies 200R and 200L go through their rotation, ears 12 are picked up from the ear die/anvil station 230/232 and rotate about the rotator 200, while every rotating puck 234B also rotates radially during rotation of the rotator 200. The ears are then deposited onto chassis web and bonded thereto, for instance by ultrasonic bonding ring, where the resulting product is sent downstream for further processing.

Again in this embodiment commutation pipes 38 extend between and are coupled to a vacuum port plate 130 and the article carrying structure 36. Together, the commutation pipes 38, vacuum port plate 46 and the article carrying structure 36 of the puck 16 are rotated and supplied with vacuum as previously described. A rotating body coupling structure 120 is provided for attaching to the rotating unit 200.

The rotation and operation of the non-rotating pucks 234A and rotating pucks 231B are described in U.S. application Ser. No. 12/925,033, and U.S. Pat. Nos. 8,172,977, 8,106,972, and 7,780,052, each of which is incorporated by reference.

Figures 15, 16:
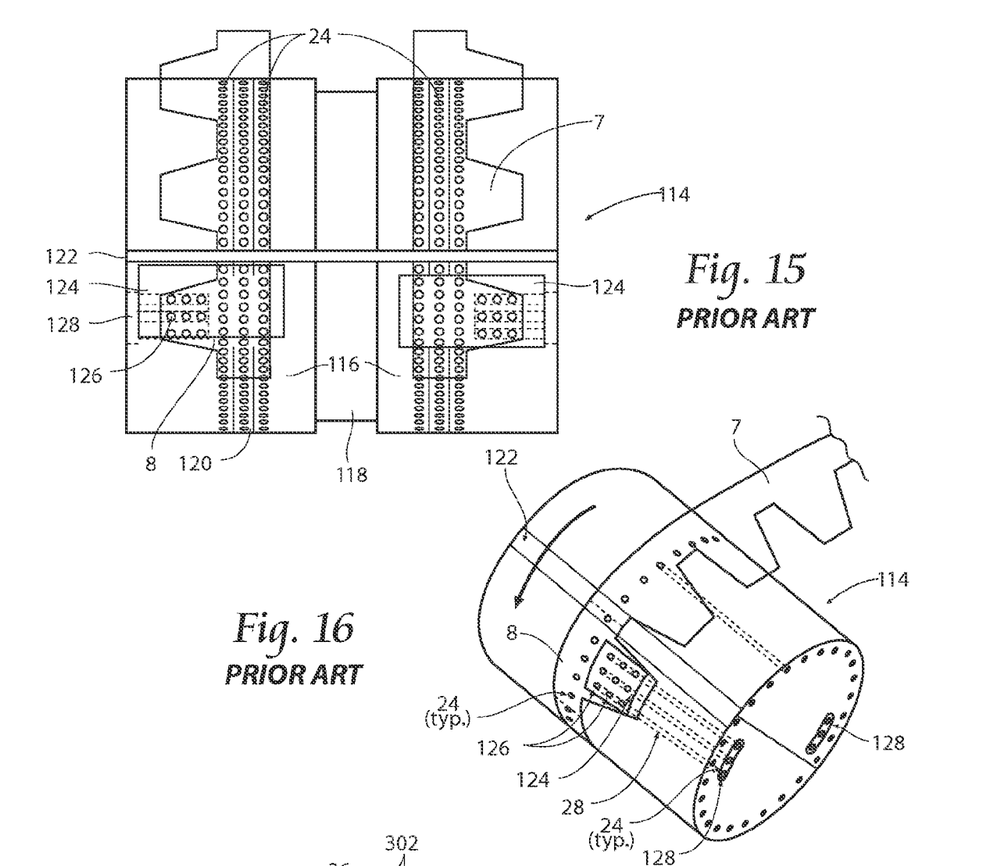
FIG. 15 is a ported vacuum drum with ear retaining portions of the prior art.
FIG. 16 is a side view of a vacuum drum of the prior art.

Referring now to FIG. 15, a ported vacuum drum (or anvil roll) with ear retaining portions of the prior art is shown. Anvil roll 114 is shown carrying ear forming material 7 (and later, after being severed, individual ears 8) in phantom. The anvil roll 114 is formed with two vacuum portions 116 separated by a center groove portion 118. The vacuum portions 116 are preferably mirror images of each other. The anvil roll 114 is symmetrical about a center plane through its circumference. Each vacuum portion 116 contains several circumferential rows of circular vacuum holes 24. Each vacuum portion 116 may also contain a circumferential groove 120 with an additional circumferential row of vacuum holes 24 located in the circumferential groove 120.

Referring now to FIG. 16, a side view of the anvil 114 of the prior art is shown. The vacuum slot 128 contains a plurality of vacuum holes 24 that allow commutation of the vacuum to the entire ear vacuum hole pattern 126, allowing the pattern 126 to be activated simultaneously, as opposed to each of the rows that comprise the vacuum of vacuum holes 24 being enabled one at a time. The vacuum pattern 126 is activated utilizing drilled ports 28 that communicate the vacuum from the slot 128 to the individual holes 24 of the pattern 126. It should be noted that the pattern 126 can also be provided with a depressed slot configuration so that it too is all simultaneously enabled with vacuum. The remaining vacuum holes 24 provided on the anvil roll 114 are enabled sequentially, by known vacuum commutation method utilizing cross drilled ports 28.

Improvements to the prior art drums for carrying webs either continuous or of discrete pieces such as ears 8 of FIGS. 15 and 16 are described in FIGS. 17-29.

Figure 17:
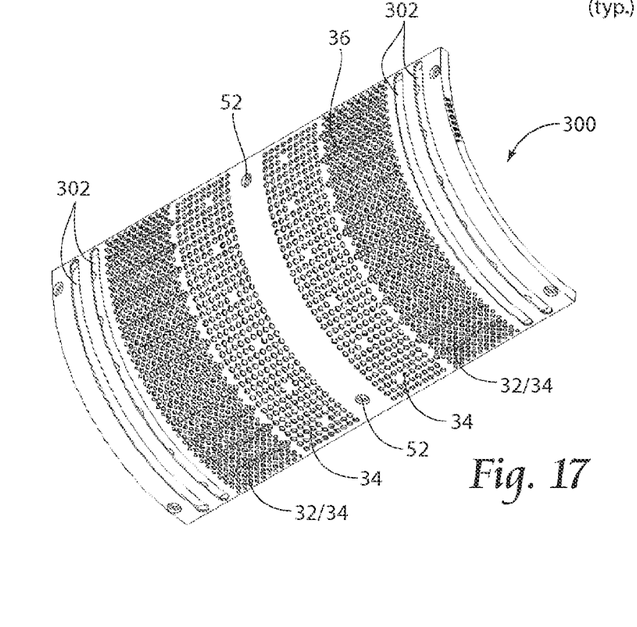
FIG. 17 is a perspective view of a ventilated shell structure of the present invention for mounting to a drum to form a continuous ventilated drum surface.
Figures 18A, 18B, 19:
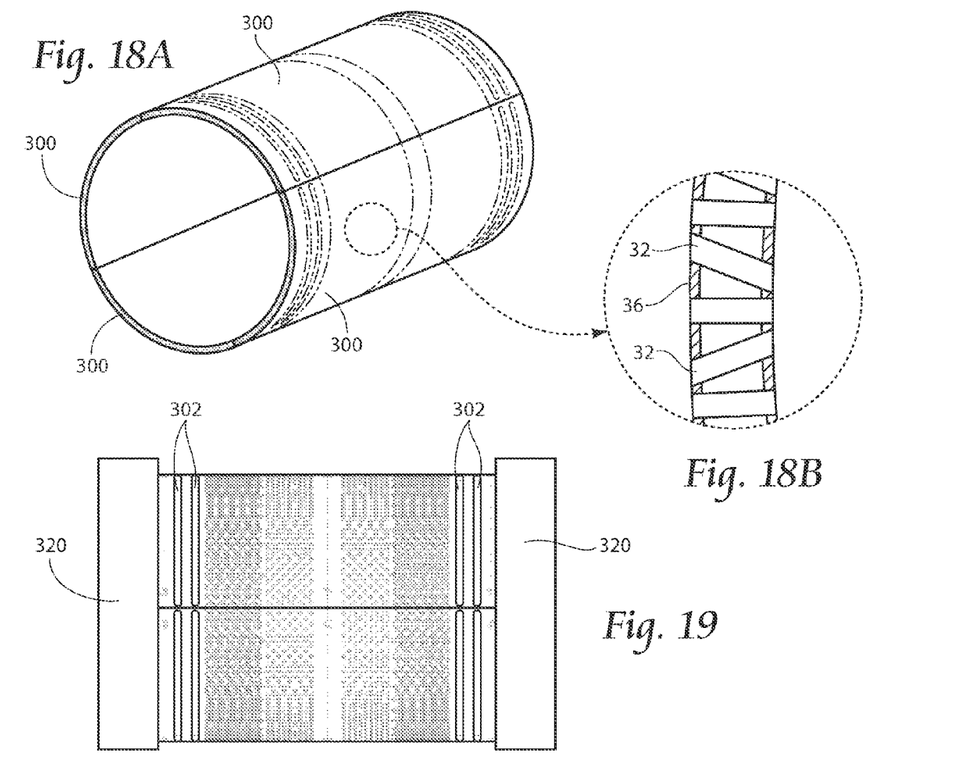
FIGS. 18a and 18b are a perspective view, with an exploded portion, of assembled ventilated shell structures of FIG. 17.
FIG. 19 is a front view of assembled ventilated shell structures of FIG. 17, showing vacuum manifolds adjacent both sides of the assembled drum, and ventilation provided through the shell surface (outside of a product contact region(s)
Figure 20:
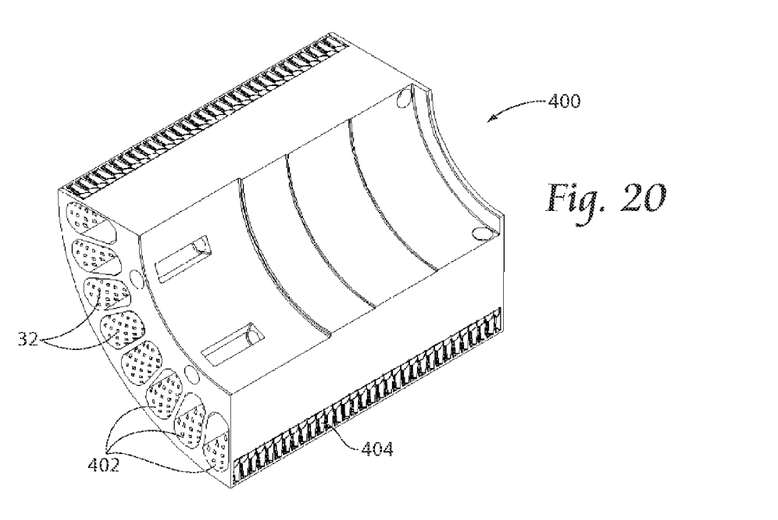
FIG. 20 is a rear perspective view of an alternate embodiment of a ventilated shell structure with a nested ventilation and vacuum commutation construction.

Referring now to FIGS. 17-19, a top vented transfer roll shell 300 is disclosed. Shell 300 is mounted to a rotating body (not shown) to form a continuous ventilated drum surface. In cases where there are vacuum manifolds 320 adjacent both sides of the drum (see, e.g., FIG. 19), side ventilation is not possible, therefore ventilation is provided through the shell surface 36 outside of the product contact region(s). In this embodiment vent channels 302 are provided, preferably at outer edges of the top vented transfer roll shell 300. Air passes under the article carrying surface 36 from the vent channels 302 underneath the surface 36 to both a first zone of air supplying vents 34/and commutation ports 32, and to a zone of exclusively air supplying vents 34. Vacuum is drawn from the vacuum manifolds 320 at the under surface of the shell 300, and through commutation ports 32 as shown in cross section at FIG. 18B. The arrangement of air supplying vents 34 and commutation ports 32 can be varied and patterned based on the configuration of the pieces intended to be carried. The ventilated shell 300 contains nested ventilation and vacuum commutation construction through the article carrying surface.

As can be seen in FIG. 18A, a plurality of top vented transfer roll shells 300 can be provided to create a vacuum roll or drum. In the depicted embodiment, four top vented transfer roll shells 300, are provided, each accounting for 90 degrees of the periphery of the drum.

Figures 21, 22A, 22B, 23:
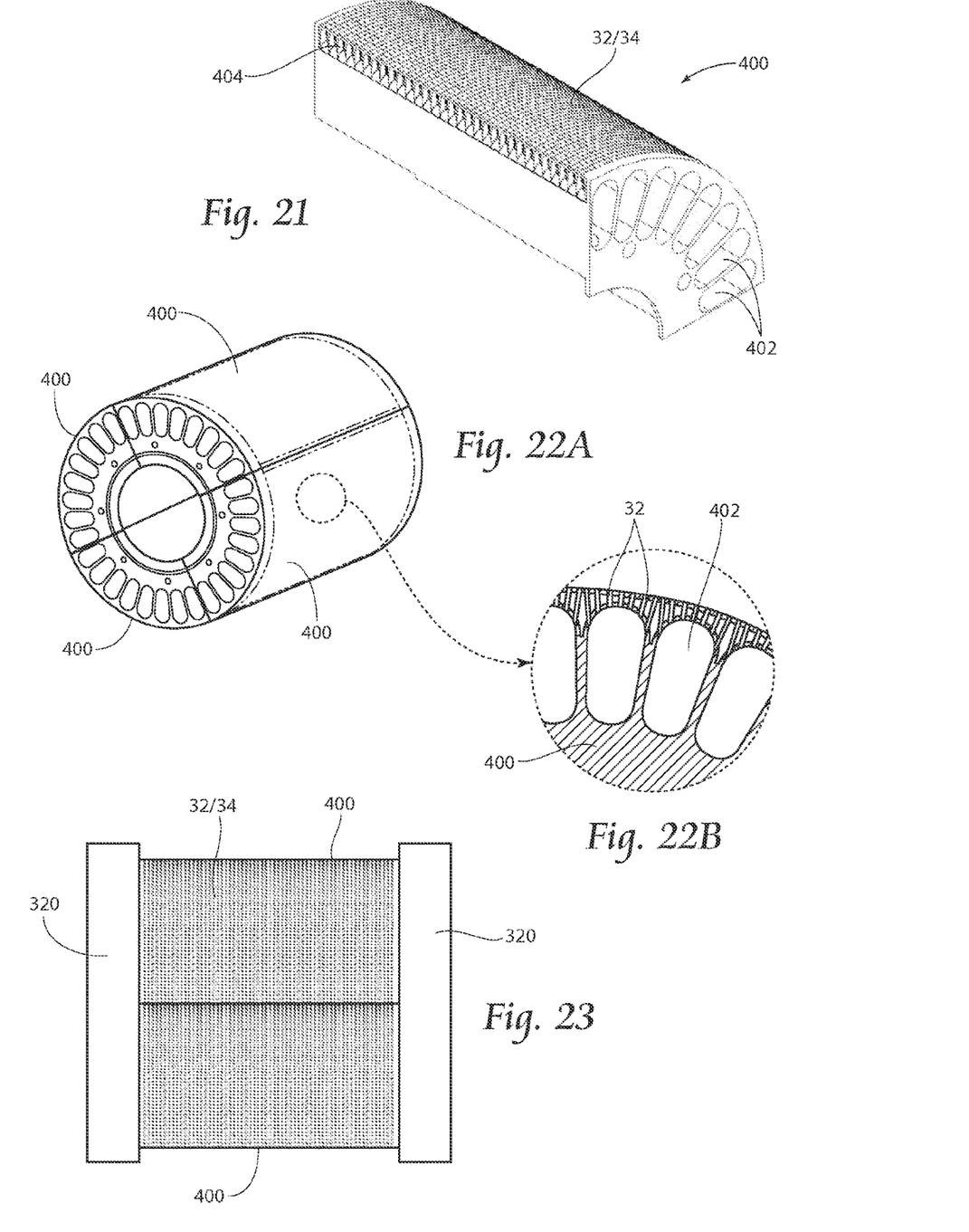
FIG. 21 is a top perspective view of the ventilated shell structure of FIG. 20.
FIGS. 22a and 22b are a perspective view, with an exploded portion, of assembled ventilated shell structures of FIG. 20.
FIG. 23 is a front view of assembled ventilated shell structures of FIG. 20, showing vacuum manifolds adjacent both sides of the assembled drum, and ventilation provided through the shell surface (outside of a product contact region(s)

In FIGS. 20-23, top vented vacuum ring 400 is disclosed, for use where vacuum manifold 320 is adjacent to sides of a drum formed by the rings 400 precludes side ventilation (see FIG. 23). In this embodiment, vacuum applied from the sides of the ring 400 through vacuum commutation channels 402 allows vacuum to be pulled through commutation ports 32 from the surface of the commutation ports 32 exposed to the interior of the ring 400, and through the ports 32 to the exterior article carrying surface of the ring 400. A plurality of air supplying vents 40 are supplied at the surface of the ring 400, so that the surface of the ring will contain an arrangement of both vents 40 and commutation ports 32. Venting and air supply is first from the outside of the shell surface outside of product contact regions, next through channels 404 to underneath product contact regions, next out through vents 40 underneath product contact regions and next drawn into ports 32.

Figures 24, 25:
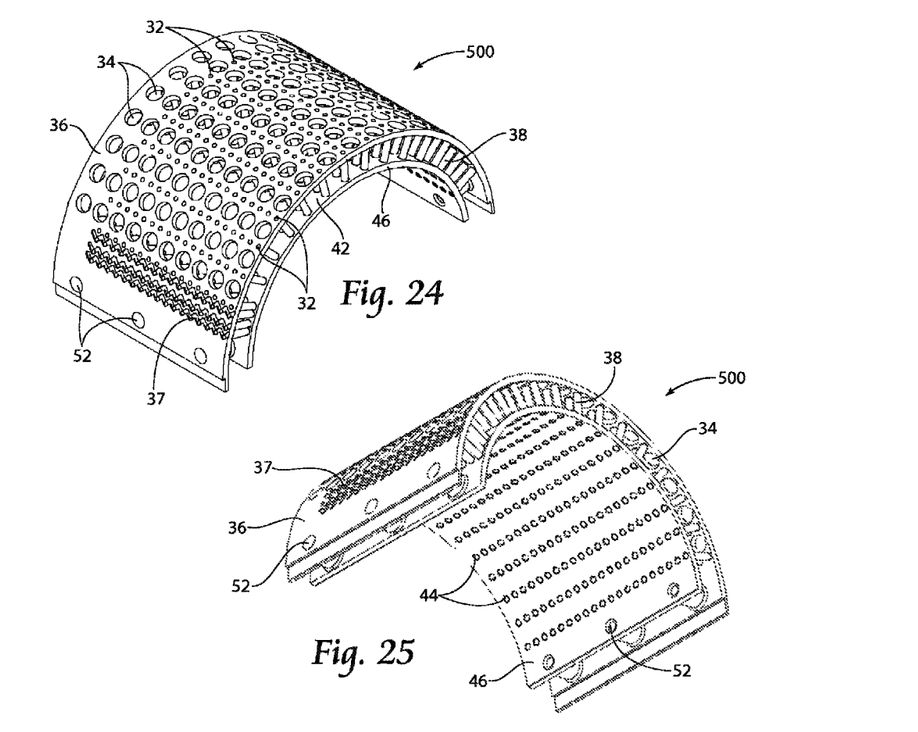
FIG. 24 is a top perspective view of a second alternate ventilated shell structure of the present invention.
FIG. 25 is a bottom perspective view of the ventilated shell structure of FIG. 24.
Figure 26:
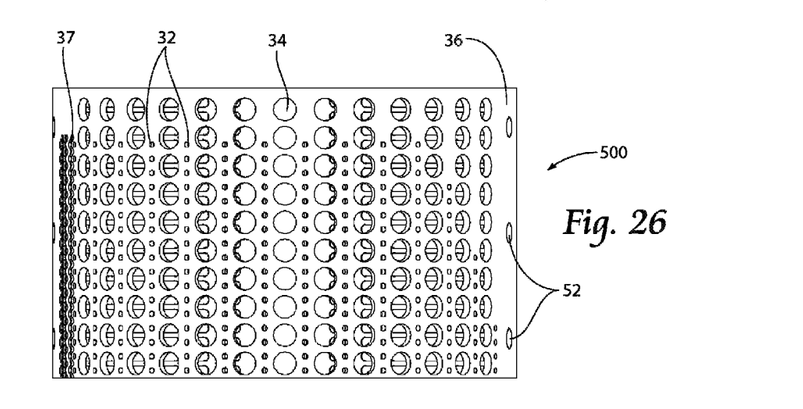
FIG. 26 is a to view of the ventilated shell structure of FIG. 24.

In FIGS. 24-26, a top and side vented vacuum pattern plate 500 is disclosed similar in construction to pucks previously described. Commutation ports 32 are provided on article carrying surface 35 coupled with commutation pipes 38. A secondary zone of aggressive channeled and interconnected ports 37 are also coupled commutation pipes 38 between article carrying surface 36 and vacuum port plate 46.

Figures 27, 28:
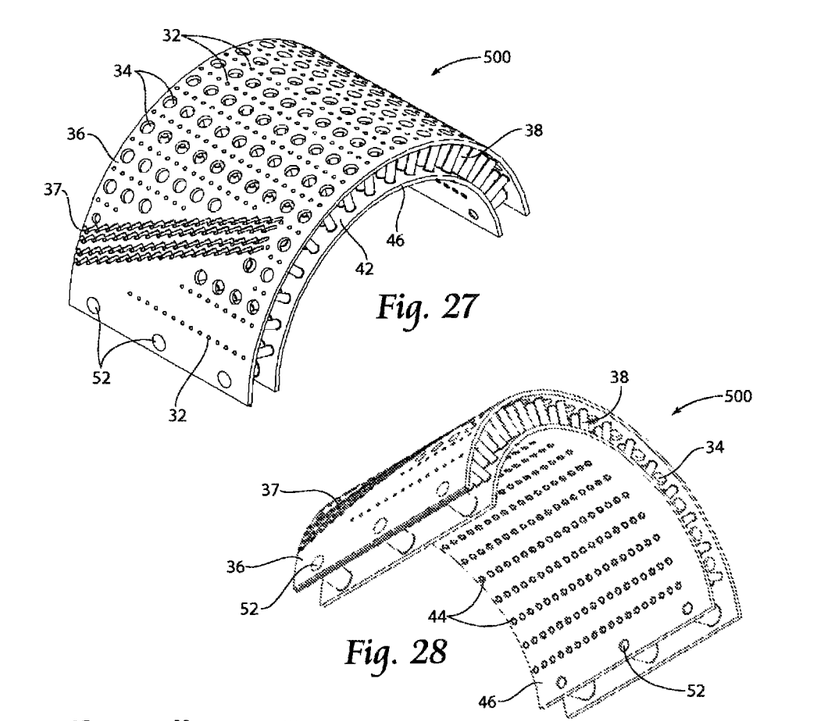
FIG. 27 is a top perspective view of a third alternate ventilated shell structure of the present invention, showing a patterned vacuum commutation port configuration.
FIG. 28 is a bottom perspective view of the ventilated shell structure of FIG. 27.
Figure 29:
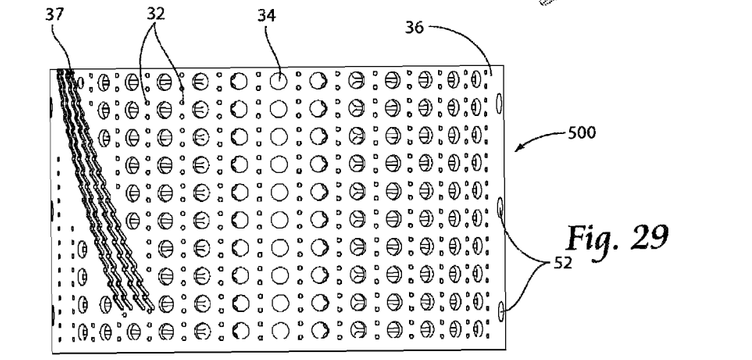
FIG. 29 is a top view of the ventilated shell structure of FIG. 27.

FIGS. 27-29 show a similar top and side vented vacuum pattern plate 600, showing a patterned vacuum commutation port 32 configuration.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A structure for carrying portions of a disposable article, said structure comprising:
    an article carrying structure comprising an underside and an article carrying face;
    a plurality of vacuum commutation pipes coupled to a source of vacuum;
    a plurality of vacuum void spaces on said article carrying face of said article carrying structure, said vacuum void spaces coupled to said vacuum commutation pipes;
    air supply void spaces on said article carrying face of said article carrying structure,
    an open sidewall structure positioned between said underside and said article carrying face, said open sidewall structure allowing passage of air to said air supply void spaces.

2. A structure according to claim 1, said structure further comprising a vacuum port plate coupled to said vacuum commutation pipes.

3. A structure according to claim 2, said vacuum port plate comprising port plate vacuum void spaces coupled to said source of vacuum.

4. A structure according to claim 1, said structure carried by a rotating body for rotating said structure in an orbital fashion about a first axis.

5. A structure according to claim 4, said structure further carried by a secondary rotating body for rotating said structure rotationally about a second axis.

6. A structure according to claim 1, said vacuum void spaces positioned adjacent said air supply void spaces.

7. A structure according to claim 1, said vacuum void spaces receiving air from said air supply void spaces.

* * * * *